United States Patent [19]
Cohen

[11] Patent Number: 6,075,051
[45] Date of Patent: *Jun. 13, 2000

[54] METHOD FOR PROTECTING PLANTS FROM FUNGAL INFECTION

[75] Inventor: Yigal Cohen, Kiryat Ono, Israel

[73] Assignee: Agrogene Ltd., Kiryat Ono, Israel

[*] Notice: This patent is subject to a terminal disclaimer.

[21] Appl. No.: 09/181,747

[22] Filed: Oct. 29, 1998

Related U.S. Application Data

[63] Continuation-in-part of application No. 08/658,636, filed as application No. PCT/US94/14108, Dec. 9, 1994, Pat. No. 5,830,919.

[30] Foreign Application Priority Data

Dec. 12, 1993 [IL] Israel ................................ 107992
Apr. 28, 1994 [IL] Israel ................................ 109474
Nov. 30, 1994 [IL] Israel ................................ 111824

[51] Int. Cl.$^7$ ..................... A01N 37/44; C07C 229/00
[52] U.S. Cl. ................ 514/561; 514/538; 514/551; 514/563; 560/42; 562/442; 562/553
[58] Field of Search ................ 514/561, 538, 514/551, 563; 560/42; 562/442, 553

[56] References Cited

U.S. PATENT DOCUMENTS

| | | |
|---|---|---|
| 3,899,585 | 8/1975 | Misato et al. . |
| 3,991,208 | 11/1976 | Dudzinski et al. . |
| 4,481,219 | 11/1984 | Watkinson . |
| 5,096,700 | 3/1992 | Seibel et al. . |
| 5,830,919 | 11/1998 | Cohen ........................ 514/561 |

FOREIGN PATENT DOCUMENTS

| | | |
|---|---|---|
| 1120802 | 7/1962 | Germany . |
| 1048507 | 11/1965 | United Kingdom . |

OTHER PUBLICATIONS

O.M. van Andel; Investigation of Plant Chemotherapy—II. Influence of Amino Acids on the Relation Plant Pathogen; T. Plzickten 64 (1958): pp. 307–327.

Fungicides An Advanced Treatise; Chemistry and Physiology, vol. II, 1969; pp. 549–551, 573, 577.

Y. Cohen; Local and Systemic Control of Phytophthora in Tomato Plants by DL–3–Amino–N–Butanoic Acids; The American Phytopathological Society, vol. 84, No. 1, 1993, pp. 55–59.

Y. Cohen et al; Systemic Translocation of $^{14}$C–DL–3Aminobutyric Acid in Tomato Plants in Relation to Induced Resistance Against Phytophthora Infestans; Physiological & Molecular Plant Pathology, (1994) 45, 441–456.

Y. Cohen et al; Beta–Aminobutyric Acid Induces the Accumulation of Pathogenesis–Related Proteins in Tomato (*Lycopersicon esculentum* L.) Plants . . . ; Plant Physiol. (1994) 104: 59–66.

A.J.P. Oort et al; Aspects of Chemotherapy; Laboratory of Phytopathology, Agricultural University; 1960, pp. 981–992

Y. Cohen; 3–Aminobutyric Acid Induces Systemic Resistance Against Peronospore Tabacina; Physiological and Molecular Plant Pathology (1994) 44, 273–288.

J. Li et al; Induction of Resistance of Cotton Plants . . . and Methyl Jasmonate; Journal of Plant Diseases and Protection, vol. 103(3), 288–299, 1996.

G. C. Papavizas et al; Effect of Amino Compounds and Related Substances Lacking Sulfur . . . of Peas; Phytopathology, vol. 53, pp. 116–122, 1963.

J. Y. Sunwoo et al; Induced Resistance Against Phytophthora Capsici . . . Acid; European Journal of Plant Pathology, vol. 102, 1996, pp. 663–670.

G. C. Papavizas; Comparison of Treatments Suggested for Control of Aphanomyces Root Rot of Peas; Plant Disease Reporter; vol. 51, No. 2, (1967), pp. 125–129.

W. A. Ayers et al; An Exocellular Pectolytic Enzyme of Aphanomyces Euteiches; Phytopathology; 55:125–248; 1965; pp. 249–253.

Mode of Action of L–Threo–Beta–Phenylserine as a Chemotherapeutant . . . ; Nature, vol. 211, pp. 326–327; 1966.

G. C. Papavizas; Greenhouse Control of Aphanomyces Root of Peas . . . Acid; Plant Disease Reporter; vol. 48, No. 7; 1964, pp. 537–541.

G. C. Papavizas et al; Effect of Sulfur–Containing Amino Compounds and Related Substances . . . of Peas; Phytopathology, vol. 53, pp. 109–115; 1963.

*Primary Examiner*—Shailendra Kumar
*Attorney, Agent, or Firm*—Browdy and Neimark

[57] ABSTRACT

A method for protecting a crop against fungal diseases by inducing local and systemic resistance of the crop comprising applying to the crop or its locus a composition containing an effective amount of at least one β-aminobutyric acid or β-amino valeric acid and salts and derivatives thereof.

84 Claims, No Drawings

METHOD FOR PROTECTING PLANTS FROM FUNGAL INFECTION

CROSS-REFERENCE TO RELATED APPLICATIONS

This application is a continuation-in-part of application Ser. No. 08/658,636, filed Jun. 5, 1996 now U.S. Pat. No. 5,830,919 which is a continuing application of PCT/US94/14108, filed Dec. 9, 1994, the entire contents of these applications are hereby incorporated by reference.

FIELD OF INVENTION

The present invention concerns a novel method to protect plants from pathogenic attack. The present invention more particularly concerns a method of applying selected non-fungicidal compounds and compositions to a crop and its locus to immunize, vis induce local and systemic resistance of the crop against fungal diseases, wherein such action is referred to in this application as "induced plant defense" (hereinafter IPD). Such compounds lack any anti-fungal activity when applied directly to the fungus, but when applied to a crop, they enhance its own immunization capacity via altering its metabolism.

BACKGROUND OF THE INVENTION

IPD (also known as SAR, Systemic Acquired Resistance) in a crop results from altered metabolism of plant tissue and is manifested by various defense mechanisms, including the accumulation in the crop of soluble proteins referred to as pathogenesis-related (PR) proteins. Some PR proteins have been shown to be hydrolytic enzymes, such as chitinases and $\beta$-1,3-glucanases, while others are shown to peroxidases. Also accumulated are a group of these proteins having a molecular weight of about 10 to 20 kDa, referred to as P14 proteins, which are now known to be anti-fungal. All or part of these proteins are believed to participate in the defense systems of a crop. Various isonicotinoyl-pyridinyl-hydrazine-derivatives, such as 2,6, -dichloroisonicotinic acid (INA), and benzothiadiazole compounds, such as Ciba-Geigy (CGA 245704), have been described in the patent literature as immunizing healthy plants against fungal diseases (European Patent Publication Numbers 268 775, 0 288 976; and 313 512). The use of threo-DL-$\beta$-methylaspartic acid and of DL-$\beta$-aminobutyric acid for the control of root rot of peas caused by *Aphanomyces euteiches* Drechs has also been described (Papavizas, *Plant Disease Reporter* 48:537–541, 1964; Papavizas, Plant Disease Reporter 51:125–129, 1967).

The use of D-alanine, D- and DL-leucine and DL-$\alpha$-aminoisobutyric acid at 0.03 M was described to reduce scab in apple caused by Venturia inaequalis (Kuc et al., Phytopathology 49:313–315, 1959).

Van Andel showed (*Tijdschur. Plantenziekten* 64:307–327, 1958) that DL-serine, D-serine (and to a lesser extent L-serine), phenylserine, DL-threonine, but not DL-$\alpha$-aminobutyric acid nor DL-$\beta$ aminobutyric acid, behaved as chemotherapeutants against the fungus *Cladosporium cucumerinum* on cucumber (ibid. page 318).

Oort and van Andel (Mededel Landbourhoogeschool Opzockkinssta, *Staat Gent.* 25:981–992, 1960) showed that DL-$\beta$-aminobutyric acid applied to leaves of tomato protected those leaves against *Phytophthora infestans* (ibid., page 987).

Various derivatives of DL-$\beta$-aminobutyric acid and $\beta$-aminocrotonic acid have been described in the patent literature as fungicides against *P. infestans* in tomato and *Plasmopara viticola* in grape (German Patent No. 1,120, 802).

Recently, Cohen et al (*Plant Physiol.*, 104:58–66, 1994) reported that PR proteins are involved in IPD in tomato.

Systemic Acquired Resistance is very often specific to a crop and a disease. For example, INA and CGA 245704 can immunize tobacco against the fungus *Peronospora tabacina* but not potato or tomato against *P. infestans* (Y. Cohen, unpublished). Also known in the literature is that various isomers of a compound may show different abilities to induce systemic resistance. For example, DL-$\beta$-aminobutyric acid induces resistance against Fusarium wilt in tomato, whereas $\alpha$-aminoisobutyric acid induces resistance against powdery mildew in wheat (Kalix et al, in *Modern Fungicides and Antifungal Compounds*, Lyr et al eds, Intercept, 1995). The literature also teaches that even enantiomers of the same molecule greatly differ in their IPD ability. Thus, Cohen showed (*Physiol. Molec. Plant Pathol.*, 44:273–288, 1994) that (R)-$\beta$-aminobutyric acid can immunize tobacco against *P. tabacina*, whereas (S-)-$\beta$-aminobutyric acid cannot. Oort and Van Andel concluded: "We do not understand why one of two related amino acids has an evident effect and the other has not, and why one influences a given plant pathogen combination but has no or hardly any influence on another" (op. cit., page 987).

The method of the present invention is not obvious in view of the prior art cited for the following reasons:

1. Oort and van Andel showed that BABA (DL-$\beta$-aminobutyric acid) applied exclusively to the leaves of tomato two days before inoculation reduced infection with *P. infestans* (ibid., page 987, line 5). The present invention shows that BABA protects plants against disease when applied to either the leaves or to the roots, or even injected to the stem, and may be applied either before or after inoculation. Also the data of Oort and van Andel are merely qualitative, as no BABA concentration or percent protection are given.

2. U.S. Pat. No. 3,899,585 (Misato et al; Aug. 12, 1975) teaches in Table 1 that Test Compound No. 13 (which is the closest to the present invention), 2-aminobutyric acid lauryl ester hydrochloride, applied to rice leaves reduces rice blast disease. The present invention teaches that 2-aminobutyric acid was totally ineffective in reducing diseases in various crops (see Cohen, *Phytopathology* 83:55–59, 1994; Cohen, *Physiol. Molec. Plant Pathol.* 44:273–288, 1994). It also teaches that Test Compound No. 13 should be applied preventively, rather than curatively, unlike the present invention which allows application of the test compound curatively. Interestingly enough, Test Compound No. 13 is probably inactive in cucumber against downy mildew, as it is missing from Example 4 (Table 4), unlike the present invention showing that BABA is active against this disease.

3. U.S. Pat. No. 3,991,208 (Dudzinski et al, Nov. 9, 1976) teaches that a tertiary amine group attached to a 2-carbon of a long-chain alkyl and carboxyethyl group substituent of the nitrogen atom are surface compounds which are antibacterial (against Gram positive bacteria). Such compounds are not amino acids, have no effect on fungi, and do not control fungal plant diseases either directly or indirectly and, therefore, have no relevance to the present invention.

4. U.S. Pat. No. 4,481,291 (Watkinson; Nov. 6, 1984) teaches that timber decay due to fungal attack by mainly Basidiomycetes may be prevented by a composition containing a nitrogenous compound and a saccharide compound. The nitrogenous compound selected from a group consisting of DL-methionine sulfoxide, 5-hydroxy lysine HCl, and aminoisobutyric acid. The latter compound is $(CH_3)_2$—$C(NH_2)$—$COOH$ (Col. 2, line 28), which is 2-amino-isobutyric acid. According to the present invention, this compound is not suitable for inducing systematic resistance against fungal plant pathogens, but BABA does, not to say that the present invention deals with protection of live green plants and not of dead woody tissue like timber. Moreover, according to Watkinson, the composition must contain a sugar as an energy source for the fungus, whereas the present invention does not.

5. U.S. Pat. No. 5,097,700 (Seibel et al; Mar. 17, 1992) teaches that halogenated amino acid derivatives are useful antibacterial agents in humans. This prior art is, indeed, not relevant to the present invention because, first, it deals with bacterial human disease and not with fungal diseases of crop plants; second, it involves halogenated (at least one halogen atom bound to the carbon backbone at position 2) amino acids, which is not required for BABA to induce IPD.

6. GB 1,048,507 (Harinack et al.; Nov. 16, 1965) teaches that glycine derivatives are effective systemic fungicides in crop plants although they are not effective against fungus spore germination in in vitro tests (page 1, line 40). This prior art departs from the present invention due to the fact that glycine is a 2-amino acid (α-amino acid) in which the $NH_2$ group is bonded to carbon 2, while the present invention deals with 3-amino acids (β-amino acids) in which the $NH_2$ group is bound to carbon 3. According to the present invention, only 3-aminobutyric acids, but not 2-aminobutyric acids, have systemic IPD effect.

The present invention deals with compounds that protect crop plants against fungal attack via immunization, namely altering plant metabolism so that it can resist fungal colonization in its tissues. It was shown by Cohen et al (*Plant Physiology* 104:59–66, 1994) that BABA enhances the accumulation of PR proteins in tomato. This accumulation was correlated with resistance to *P. infestans*. However, this is probably not the case in other crops, such as curcurbits and tobacco, in which BABA also induces IPD response. In curcurbits BABA induces the accumulation of callose and lignin in the infected sites, which probably stops the fungus, whereas in tobacco, the IPD mechanism remains obscure (Cohen, *Physiol. Molecul. Plant Pathol.* 44:273–288, 1994).

SUMMARY OF THE INVENTION

It is the objective of the present invention to provide a novel method to induce IPD.

It is a further objective of the present invention to provide a novel method to induce IPD in selected crops.

BRIEF DESCRIPTION OF THE INVENTION

The laboratory of the present inventor has found a novel method of protecting a crop against fungal diseases caused by fungi by applying to the crop or its locus a composition containing an effective amount of a compound of Formula (I):

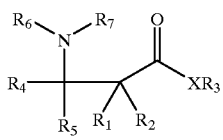

$R_1$ and $R_2$ are independently hydrogen, $C_{1-8}$ alkyl, phenyl, and phenyl $C_{1-4}$ alkyl.

$R_3$ is hydrogen, $C_{1-23}$ alkyl, carboxy $C_{1-4}$ alkyl, phenyl $C_{1-4}$ alkyl, wherein the phenyl moiety is unsubstituted or monosubstituted by halogen, or $C_{2-23}$ alkoxycarbonyl $C_{1-4}$ alkyl.

$R_4$ and $R_5$ are independently hydrogen or $C_{1-8}$ alkyl.

$R_6$ and $R_7$ are independently hydrogen, $C_{1-8}$ alkyl $C_{2-8}$ alkanoyl, phenyl $C_{1-4}$ alkyl, benzoyl, wherein the phenyl moiety is unsubstituted or monosubstituted by halogen, $C_{2-8}$ alkoxycarbonyl, $COHNR_8$, wherein $R_8$ is hydrogen, $C_{1-8}$ alkyl, phenyl, phenyl $C_{1-4}$ alkyl; phenyl $C_{2-4}$ alkyloxycarbonyl.

X is O, S or NH, and salts thereof; and the crop is selected from the group consisting of corn, cucumber, melon, broccoli, cauliflower, kohlrabi, potato, cabbage, sunflower, tobacco, grape, cotton, maize, sorghum, pearl millet, rice, lettuce, hop, avocado, citrus, soybean and onion.

DETAILED DESCRIPTION OF THE INVENTION

Alkyl, as used herein, refers to straight chains, branched and cyclic forms and, preferably, contain one to four carbon atoms.

$R_1$ and $R_2$ are preferably independently hydrogen, methyl or phenyl. More preferably, $R_1$ is hydrogen or methyl, and $R_2$ is hydrogen.

$R_3$ is preferably hydrogen.

$R_4$ and $R_5$ are preferably independently hydrogen or $C_{1-3}$ alkyl. More preferably, $R_4$ is hydrogen or methyl, and $R_5$ is hydrogen or $C_{1-3}$ alkyl. More preferably, $R_4$ is hydrogen or methyl, and $R_5$ is hydrogen.

$R_6$ and $R_7$ are preferably independently hydrogen, $C_{1-5}$ alkyl, benzyl optionally substituted by halogen. More preferably, $R_6$ is hydrogen or methyl, and $R_7$ is hydrogen.

X is preferably oxygen.

Preferred compounds of the invention are the β-aminobutyric acids and the β-aminovaleric acids; and most preferred is R-β-aminobutyric acid. The structures of various aminobutyric acids are shown in Scheme 1.

Scheme 1:
Aminobutyric Acids

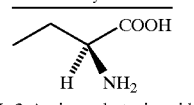
L-2-Amino-n-butyric acid

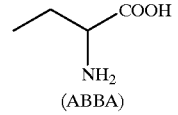
(ABBA)
DL-2-Amino-n-butyric acid

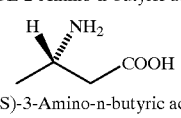
(S)-3-Amino-n-butyric acid

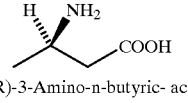
(R)-3-Amino-n-butyric- acid

-continued

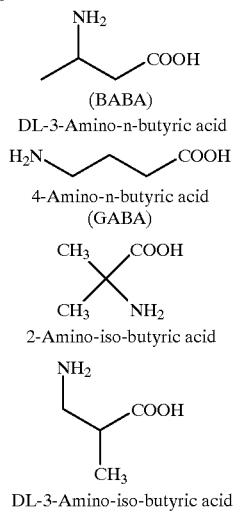

(BABA)
DL-3-Amino-n-butyric acid

4-Amino-n-butyric acid
(GABA)

2-Amino-iso-butyric acid

DL-3-Amino-iso-butyric acid

Salt forms of the compound of formula (I) contemplated in this application include acid addition salts, such as those obtained by the addition of HCl, CF$_3$, CO$_2$H, toluene sulfonic acid, methane sulfonic acid and (CO$_2$H)$_2$

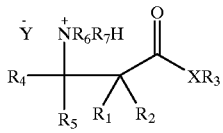

wherein Y is the residue of the acid;
alkali metal salts, such as those obtained by treatment with NaOH, KOH or LiOH

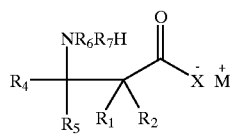

wherein M is an alkali metal, such as Na, K or Li; and acid addition/amine salts such as those obtained by treatment with HCl and an amine, such as diethylamine, propyl amine, benzylamine

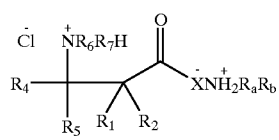

wherein $R_a$ and $R_b$ are substituents.

Preferred crops in which the method of the present invention is applicable are cucumbers, melon, broccoli, cauliflower, kohlrabi, potatoes sunflower, tobacco, grape, cotton, maize, sorghum, cabbage, pearl millet, rice, onion and hop. Most preferred are sunflower, grape, cucumber, melon, broccoli, kohlrabi, cauliflower, potato, tobacco and maize.

Production Methods

The novel compounds encompassed by the present application are structurally related to known compounds and can be easily prepared by either derivatizing the known compounds or by modifying the procedures for preparing the known compound, as required. These procedures will be apparent to those skilled in the art. The following procedures are illustrative.

Compounds of Formula (Ia):

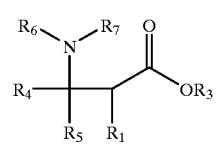

wherein $R_1$ and $R_{4-7}$ are as previously defined, and $R_3$ represents hydrogen or $C_{1-8}$ alkyl can be obtained from a compound of the formula (IIa):

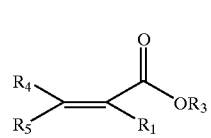

To prepare compounds of formula (Ia) where $R_6$ is H and $R_7$ is as previously defined, the compound of formula (IIa) is reacted with NR$_7$H$_2$, wherein $R_7$ is as previously defined. Reactions of this type are described in the literature, e.g., Zilkha and Rivilin, *J. Org. Chem.* 23:94 (1957).

To prepare compounds of formula (Ia) where $R_6$ and $R_7$ are as previously defined but excluding hydrogen, the compound of formula (IIa) is reacted with NR$_6$R$_7$Li, wherein $R_6$ and $R_7$ are as previously defined but excluding hydrogen. Reactions of this type are described in the literature, e.g., Davies et al, *Tetrahedron: Asymmetry* 2(3):183–186 (1991).

Compounds of the formula (IIa) are either known or obtainable from known compounds according to standard procedures.

As can be appreciated, in such cases where $R_4$ and $R_5$ do not represent the same substituent, the carbon atom to which they attach is chiral. Procedures for preparing each enantiomer form are either specifically described in the literature, e.g., EP 0 144 980 or Davies supra, or can be prepared according to analogous procedures.

The present method was found to be effective against a variety of diseases. Examples are late blight, downy mildew, blue mold, leaf spots, fusarium wilt, trunk rot, fruit brown rot, damping off, white rust, black shunk and Phytophthoras root rots.

The compounds of this invention will typically be applied to crops or their locus before or after the onset or after the initial signs of fungal attack and may be applied to the foliar surfaces of the crop. The amount of the active ingredient to be employed will be sufficient to induce the systemic resistance of the crop to control the fungi and will vary depending on such factors as the species of fungi to be controlled, the type of treatment (for example, spraying, dusting, seed treatment, soil drench), the condition of the crop, and the particular active ingredient used.

As an application to the crop or its locus the compounds will be applied to the crops with a dosage rate of from 0.1 to 5 kg/ha, preferably from 0.2 to 2 kg/ha, with application being repeated as necessary, typically at intervals of every one to three weeks.

Depending on circumstances, the compounds of this invention may be used in association with other pesticides, e.g., fungicides, insecticides, acaricides, herbicides, or plant growth regulating agents, in order to enhance their activity or to widen their spectrum of activity.

The compounds of this invention are conveniently employed as fungicidal compositions in association with agriculturally acceptable carriers or diluents. Such compositions also form part of the present invention. They may contain, aside from a compound of formula (I) as active agent, other active agents, such as fungicides. They may be employed in either solid or liquid application forms, e.g., in the form of a wettable powder, an emulsion concentrate, a water dispersible suspension concentrate ("flowable"), a dusting powder, a granulate, a delayed release form incorporating conventional carriers, diluents and/or adjuvants. Such compositions may be produced in conventional manner, e.g., by mixing the active ingredient with a carrier and other formulating ingredients.

Particular formulations to be applied in spraying forms, such as water dispersible concentrates or wettable powders, may contain surfactants, such as wetting and dispersing agents, e.g., the condensation product of formaldehyde with naphthalene sulphonate, an alkyl-aryl-sulphonate, a lignin sulphonate, a fatty alkyl sulphate, an ethoxylated alkylphenol and an ethoxylated fatty alcohol.

In general, the formulations include from 0.01 to 90% by weight of active agent, said active agent consisting of either of at least one compound of formula (I) or mixture thereof with other active agents, such as fungicides. Concentrate forms of compositions generally contain between about 2 and 80%, preferably between about 5 and 70% by weight of active agent. Application forms of the formulation may, for example, contain from 0.01 to 20% by weight, preferably from 0.01 to 5% by weight, of the active agent.

Formulation Example I: Wettable Powder 50 parts by weight of a compound of formula (I) are ground with two parts of lauryl sulphate, three parts sodium lignin sulphonate, and 45 parts of finely divided kaolinite until the mean particle size is below 5 microns. The resulting wettable powder so obtained is diluted with water before use to a concentration of between 0.01 to 5% active ingredient. The resulting spray liquor may be applied by foliar spray, as well as by root drench application.

Formulation Example II: Emulsion Concentrate 25 parts by weight of a compound of formula (I), 65 parts of xylene, 10 parts of the mixed reaction product of an alkylphenol with xyleneoxide and calcium-dodecyl-benzene sulphonate are thoroughly mixed until a homogeneous solution is obtained. The resulting emulsion concentrate is diluted with water before use.

Formulation Example III: Granulate (for soil treatments)

0.5 parts by weight of a binder (non-ionic tenside)is sprayed onto 94.5 parts by weight of quartz sand in a tumbler mixer and is thoroughly mixed. Five parts by weight of a compound of formula (I) in powdered form are then added and thoroughly mixed to obtain a granulate formulation with a particle size in the range of from about 0.3 to about 0.7 mm. The granulate may be applied by incorporation into the soil adjacent the plants to be tested.

Formulation Example IV: Seed or Tuber Dressing 25 parts by weight of a compound of formula (I), 15 parts of dialkylphenoxy-poly-(ethylenoxy) ethanol, 15 parts of fine silica, 44 parts of fine kaolin, 0.5 parts of a colorant (e.g., crystal violet) and 0.5 parts of xanthan gum are mixed and ground in a contraplex mill at approximately 10,000 rpm to an average particle size of below 20 microns.

The resulting formulation is applied to the seeds or tubers as an aqueous suspension in an apparatus suitable for that purpose. Where the compound of formula (I) is liquid, it is first absorbed on the carriers,if desired, with the aid of a small amount of a volatile solvent, such as acetone. The resulting powder is first allowed to dry, if a solvent is used, then the other ingredients are added, and the rest of the procedure is carried out.

Formulation Example V: Soil Drench Drip Irrigation

Two parts by weight of a compound of formula (I) are dissolved in 1,000 parts of water. The resulting formulation is applied to plants by drip irrigation.

As previously mentioned, the compounds of formula (I) are effective in activating or enhancing a crop's defense system against fungal diseases caused by fungi. Such activity can be demonstrated in using the general procedures of the following tests.

Test A: IPD in Potato Plants against *P. infestans*. Potato plants (cultivar Bintje) are grown from tubers in pots filled with sandy loam, peat and perlite mixed in equal volumes, in a greenhouse (20–22° C.). The plants are ready for testing when they have 6 or 7 compound leaves.

Tests are carried out with the metalaxyl-resistant isolate MR1 of *P. infestans*, as well as the MS2, MS3, MR2 and MR3 isolates (Kadish and Cohen, *Phytopathology* 78:912–915, 1988). The fungus is grown on potato tuber slices at 15° C. in the dark. Fresh sporangia are harvested at 6 days after inoculating the slices into double distilled water (4° C.) and adjusting their concentration to 10,000 sporangia/ml before use for challenge inoculations.

The compounds of this application are dissolved in water and sprayed on either the lower or upper leaf surfaces of the potato plants with a fine atomizer (about 10 ml per plant). The plants are left on the bench until the droplets dry and are then placed in a growth cabinet calibrated to 20° C. and 14 hours of light per 10 day.

Challenge inoculation with *P. infestans* is carried out at time intervals ranging from 30 minutes to 12 days after treatment with the compounds by spraying a sporangial suspension on the upper leaf surfaces (about 15 ml per plant). In one experiment, inoculum droplets (10 containing about 100 sporangia) are placed on the leaf surfaces, two droplets per leaflet, one on each side of the main vein. In another experiment, the compounds are applied curatively, 24 hours after inoculation with *P. infestans.*

Inoculated plants are kept at 100% RH in the dark for 24 hours at 18° C. and then returned to a growth cabinet maintained at 20° C. with 12 hours of light per day. Disease severity is monitored 4–8 days after inoculation by visually estimating the proportion of a leaf area covered by blight lesions.

Test B: IPD in Tobacco Plants against *P. tabacina*. Tobacco plants (cultivars Ky-14 or Ky-16) are grown from seed in pots in a greenhouse. When reaching the 10-leaf stage or older, the compounds of this application are injected into the stem of the plant. At 1–3 days before injection or at 1–10 days after injection, plants are challenge-inoculated with conidia of the fungus *P. tabacina* Adam, which causes the blue mold disease. Conidia are harvested from previously infected tobacco plants. Inoculation is done with 10,000–100,000 conidia/ml, with approximately 50 ml per plant. The procedure described above for inoculation, maintaining and scoring the disease is also applicable here.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of the procedures, as well as of the principles and conceptual aspects of the invention.

EXAMPLE 1

N-(2-hydroxyethyl)-aminobutyric Acid

A solution of 86 g of crotonic acid (1 mole) and ethanolamine (1 mole) in pyridine (200 ml) is refluxed for 2–3 hours and subsequently cooled. The resulting product is filtered and recrystallized to yield the title compound having m.p. 178–180° C. (Compound 1.1, Table 1).

Following an analogous procedure, Compounds 1.1–1.7, 1.10, 1.11, and 1.13–1.15, set forth in Table 1, are obtained.

EXAMPLE 2

3-aminohexanoic Acid

A mixture of 2 hexanoic acid (7.0 g, 0.06 mole) and concentrated aqueous ammonium hydroxide (70 ml) is heated for 24 hours in an autoclave at 150° C. The cooled mixture is treated with carbon black and filtered. After evaporation of the solvent, the crude product is recrystallized from ethanol to give the title compound m.p. 203° C. (Compound 1.21, Table 1).

Following an analogous procedure, Compounds 1.8, 1.9, 1.12 and 1.18–1.20 of Table 1 are obtained.

EXAMPLE 3

N-benzoyl-3-aminobutyric Acid

To a cooled solution of 3-aminobutyric acid (13 g) in 2M NaOH (130 ml) is added benzoyl chloride (19.7 g) over the course of two hours. The mixture is allowed to warm to room temperature. Washing with diethyl ether, acidifying the aqueous phase with 20% HCl, extracting with diethyl ether, drying over $MgSO_4$, evaporating the solvent and recrystallizing in either/hexane gives the title compound m.p. 150–152° C. (Compound 1.6, Table 1).

EXAMPLE 3A

DL-N-benzoyl-3-aminobutyric Acid N-octyl-ester 3.0 g PC15 was added to 3.0 g DL-N-benzoyl-3-aminobutyric acid in 30 ml dichloromethane in small portions, keeping the mixture temperature at 5° C. The mixture was allowed to warm to 20–22° C. and stirred for five hours. Petrol ether 60–80 (150 ml) was added, the chloride was filtered and tried, yielding 2.3 g product.

To the chloride in 20 ml dichloroethane was added 4.1 g n-octanol in 10 ml dichloroethane, during 10 minutes at 20° C. The mixture was heated to 65° C. during 6 hours. After distillation, 20 ml dichloroethane was added and washed with 3×10 ml sodium bicarbonate (2%) dried over $MgSO_4$. Evaporation of the solvent gave 2.0 g of the title compound, having a molecular weight of 319.

Following an analogous procedure, Compound 1.17 of Table 1 was obtained.

TABLE 1

Compounds Prepared of the Formula

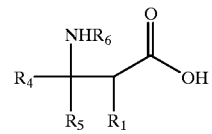

| Compound | $R_1$ | $R_4$ | $R_5$ | $R_6$ | m.p. (° C.) |
|---|---|---|---|---|---|
| 1.1 | H | $CH_3$ | H | hydroxyethyl | 178–180 |
| 1.2 | H | $CH_3$ | H | isopropyl | 167–169 |
| 1.3 | H | $CH_3$ | H | benzyl | 178–180 |
| 1.4 | H | $CH_3$ | H | cyclohexyl | 161–163 |
| 1.5 | H | $CH_3$ | H | n-hexyl | 151–153 |
| 1.6 | H | $CH_3$ | H | p-chlorobenzyl | 152–154 |
| 1.7 | H | $CH_3$ | H | benzyl | 180–182 |
| 1.8 | H | ethyl | H | H | 128–130 |
| 1.9 | H | $CH_3$ | $CH_3$ | H | 216 |
| 1.10 | $CH_3$ | H | H | benzyl | 148 |
| 1.11 | H | $CH_3$ | H | phenyl-ethyl | 164 |
| 1.12 | H | phenyl | H | H | 220–221 |
| 1.13 | H | $CH_3$ | H | n-octyl | 150 |
| 1.14 | H | $CH_3$ | H | n-decyl | 148 |
| 1.15 | H | ethyl | H | benzyl | 157–160 |
| 1.16 | H | $CH_3$ | H | benzoyl | 150–152 |
| 1.17 | H | $CH_3$ | H | benzyloxycarbonyl | 128–130 |
| 1.18 | H | ethyl | H | H | 178–180 |
| 1.19 | H | $CH_3$ | H | H | 209–210[1] |
| 1.20 | H | $CH_3$ | H | $CH_3$ | 86–87[2] |
| 1.21 | H | propyl | H | H | 203 |

[1](R) - enantiomer
[2]monohydrate

EXAMPLE 4

N-benzyloxycarbonyl-3-aminobutyric Acid (4-chlorophenyl)-1-ethylamide

Z-protected β-aminobutyric acid (0.02 ml), (4-chlorophenyl)-1-ethylamine and 1.1 equivalents of DCC (dicyclohexyl carbonimide) are stirred in ethyl acetate at room temperature for 16 hours. The precipitate is filtered, the filtrate evaporated and chromatographed on silica gel (hexane/ethyl acetate 1:1) to give the title compound as a mixture of diastereomers m.p. 168–178° C.

EXAMPLE 5

β-aminobutyric Acid Hydrochloride 5.15 g β-aminobutyric acid (50 mole) are dissolved in 650 ml methanol. After addition of 5.5 ml concentrated HCl, the solution is evaporated The residue is triturated in diethyl ether, decanted and dried. A colorless oil is isolated. Microanalysis: C-34.4; H-7.2; N-10.0; Cl-25.4.

EXAMPLE 6

β-aminobutyric Acid Sodium Salt 2.06 g β-aminobutyric acid (20 mole) are dissolved in 100 ml of a mixture of water:methanol (1:1). One equivalent NaOH in 10 ml water is added. The solution is evaporated, and the resulting amorphous solid is dried. Microanalysis: C-37.4; H-6.7; N-10.9.

EXAMPLE 7

β-amino butyric Acid Diethylammonium Chloride 1.4 g β-aminobutyric acid (10 mole) are dissolved in 100 ml of methanol. Diethylamine (0.9 g, 12. 3 mole) is added, and the residue is evaporated. The oily residue is washed with ether, decanted and dried to afford an amorphous material. H-NMR (CD$_3$ OD, 200 MHz) 1.29 (m, 9H, 3 CH$_3$; 2.25–2.45 (m, 2H, CH$_2$); 3.14 (p, 4H, CH$_2$ CH$_3$); 3.34–3.58 (m, 1H, CH).

EXAMPLE 8

Protection of Tomato Plants against Fusarium Wilt

Tomato plants were grown in sterile soil in a greenhouse. When they reached the 4-leaf stage, they were treated with a compound of the formula (I) solution by a soil drench. Four days later, the plants were uprooted, washed with water, and their root system immersed for two minutes in conidial suspension (10$^7$ conidia/ml) of the fungus *Fusarium oxysporum* f.sp. lycopersici. Plants were then transplanted (without washing) into pots filled with sterile soil. Twelve days later all challenged-control plants wilted of the disease, whereas one of the challenged-treated plants wilted. Growth of the latter plants was similar to that of the control, unchallenged-uninoculated plants. Results are shown in Table 2.

TABLE 2

Protection of Tomato Plants (cv. Rehovot - 13) against Fusarium Wilt Caused by *Fusarium oxysporum* f.sp. *lycopersici* by Aminobutyric Acids (Soil Drench)

| | Percent of Plants | |
|---|---|---|
| Compound | Healthy | Wilted |
| None | 0 | 100 |
| AABA | 34 | 66 |
| BABA | 100 | 0 |
| GABA | 7 | 93 |

Plants were soil-drenched with 2000 ppm of the compound and inoculated four days later; rating was taken 12 days after inoculation.

EXAMPLE 9

Following the method of Example 8, a similar experiment was run using a lower concentration of BABA. The results are Table 3.

TABLE 3

Protection of Tomato Plants (cv. Rehovot - 13) against Fusarium Wilt Caused by *Fusarium oxysporum* f.sp. *lycopersici* by Lower Concentrations of BABA (Soil Drench)

| Concentration O (ppm) | Percent Wilted Plants |
|---|---|
| 0 | 100 |
| 250 | 53 |
| 500 | 43 |
| 1000 | 0 |

EXAMPLE 10

Following the above-described methods, the effects of aminobutyric acids on downy mildew in sunflower was studied. The results appear in Table 4, which shows the marked activity of BABA in percent protection.

TABLE 4

The Effects of Aminobutyric Acids on Systemic Downy Mildew of Sunflowers (cv. D.I.-3) Caused by *Plasmopara halstedii*

| Compound | Method of Application | Concentration | Percent Protection |
|---|---|---|---|
| | | mg/l | |
| AABA | spray | 2000 | 10 |
| BABA | spray | 2000 | 100 |
| GABA | spray | 2000 | 0 |
| | | mg/Plant | |
| AABA | soil drench | 5 | 0 |
| BABA | soil drench | 5 | 100 |
| GABA | soil drench | 5 | 0 |
| AABA | root uptake | 2 | 0 |
| BABA | root uptake | 2 | 100 |
| GABA | root uptake | 2 | 0 |

In all experiments, inoculation with the fungus was done either one day before treatment (curative) or two days after treatment.

EXAMPLE 11

Following the above-described methods, the effects of aminobutyric acids on *P. viticola* in grape plants were studied. The results, which appear in Table 5, show good protection given by BABA.

TABLE 5

The Effects of Aminobutyric Acids on Systemic Downy Mildew Caused by *Plasmopara viticola* in Grape Plants (cv. Sauvignon Blanc or Cabernet Sauvignon)

| Concentration ppm mg/Plant | Application Mode | % Protection with | | |
|---|---|---|---|---|
| | | AABA | BABA | GABA |
| 10 | soil drench | 0 | 60 | 0 |
| 100 | spraying } | 0 | 30 | 0 |
| 200 | intact } | 0 | 60 | 0 |
| 500 | plants } | 15 | 90 | 5 |
| 1000 | in pots } | 20 | 95 | 5 |
| 10 | | 0 | 90 | 0 |
| 50 | floating } | 5 | 95 | 0 |
| 100 | leaf discs } | 10 | 100 | 5 |

Disease rating was taken 9 days after inoculation. BABA also has curative effect as follows: when applied to inoculated leaf discs at 0, 1, 2 and 3 days after inoculation percent protection of 100, 86, 50 and 30%, respectively.

EXAMPLES 12

Following the above-described methods, the effects of aminobutyric acids on downy mildew in cucumber and melon studied. The results, which appear in Table 6, show the good protection given by BABA.

TABLE 6

The Effects of Aminobutyric Acids on Downy Mildew Caused by *Pseudoperonospora cubensis* in Cucumber and Melon Plants (foliar spray) or leaf discs (floating)

| Plant & Cultivar | Concentration (ppm) | AABA | BABA | GABA |
|---|---|---|---|---|
| | | | % Protection Whole Plants | |
| cucumber (Dlila) | 250 | 0 | 0 | 0 |
| | 500 | 0 | 38 | 0 |
| | 1000 | 0 | 65 | 0 |
| | 2000 | 5 | 87 | 0 |
| melon (Galia) | 250 | 0 | 30 | 0 |
| | 500 | 0 | 38 | 0 |
| | 1000 | 0 | 86 | 0 |
| | 2000 | 0 | 92 | 0 |
| | | | % Protection Leaf Discs | |
| cucumber (Dlila) | 6 | 0 | 94 | 0 |
| | 12 | 0 | 97 | 0 |
| | 25 | 0 | 100 | 20 |
| | 50 | 0 | 100 | 60 |
| melon (Ananas) | 6 | 0 | 19 | 0 |
| | 12 | 0 | 25 | 0 |
| | 25 | 0 | 70 | 0 |
| | 50 | 37 | 85 | 30 |

Disease rating was taken 7 days after inoculation

EXAMPLES 13–15

Following the above-described methods, the effects of R-BABA and S-BABA against *Peronospora parasitica* and *Alternaria brassicicola* in broccoli, kohlrabi and cauliflower were studied; and the results, which appear in Tables 7–9, respectively, show the good protection given by R-BABA.

TABLE 7

Protection of Broccoli (cv. Shugon) against *Peronospora parasitica* and *Alternaria brassicicola* with Aminobutyric Acids Applied as a Foliar Spray

| Compound | Concentration ppm | % Protection P. parasitica | A. brassicicola |
|---|---|---|---|
| R-BABA | 125 | 33 | 0 |
| | 250 | 50 | 20 |
| | 500 | 95 | 60 |
| | 1000 | 100 | 85 |
| | 2000 | 100 | 90 |
| S-BABA | 500 | 0 | not tested |
| | 1000 | 0 | not tested |
| | 2000 | 0 | not tested |

TABLE 8

Protection of Kohlrabi (cv. White Wien) against *Peronospora parasitica* and *Alternaria brassicicola* with Aminobutyric Acids Applied as a Foliar Spray

| Compound | Concentration ppm | % Protection P. parasitica | A. brassicicola |
|---|---|---|---|
| R-BABA | 125 | 33 | 0 |
| | 250 | 50 | 20 |
| | 500 | 95 | 60 |
| | 1000 | 100 | 85 |
| | 2000 | 100 | 90 |
| S-BABA | 500 | 0 | not tested |
| | 1000 | 0 | not tested |
| | 2000 | 0 | not tested |

TABLE 9

Protection of Cauliflower (cv. Nurit) against *Peronospora parasitica* and *Alternaria brassicicola* with Aminobutyric Acids Applied as a Foliar Spray

| Compound | Concentration ppm | % Protection P. parasitica | A. brassicicola |
|---|---|---|---|
| R-BABA | 125 | 33 | 0 |
| | 250 | 50 | 20 |
| | 500 | 95 | 60 |
| | 1000 | 100 | 85 |
| | 2000 | 100 | 90 |
| S-BABA | 500 | 0 | not tested |
| | 1000 | 0 | not tested |
| | 2000 | 0 | not tested |

EXAMPLE 16

Following the above-described methods, the effects of a 25% formulated DL-BABA in potato plants was studied. The results are shown in Table 10.

TABLE 10

Effects of 25% WP Formulated DL-BABA in Potato Plants

| ppm DL-BABA | % Protection against Phytophthora Infections |
|---|---|
| Control | — |
| 31 | 0 |
| 62 | 7 |
| 125 | 67 |
| 250 | 67 |
| 500 | 81 |
| 1000 | 91 |
| 2000 | 97 |

EXAMPLE 17

Following the above-described methods, the markedly good effects of DL-BABA Against late blight in potato (Bintje) in growth chambers was studied. The results are shown in Table 11.

TABLE 11

Effects of Aminobutyric Acids against Late Blight in Potato Crops in Growth Chamber

| Compound | Days after Inoculation | % Blighted Leaf Area |
|---|---|---|
| Control | 2 | 0 |
|  | 4 | 80 |
|  | 6 | 95 |
|  | 8 | 98 |
|  | 10 | 98 |
| GABA | 2 | 0 |
|  | 4 | 60 |
|  | 6 | 85 |
|  | 8 | 90 |
|  | 10 | 98 |
| DL-AABA | 2 | 0 |
|  | 4 | 45 |
|  | 6 | 70 |
|  | 8 | 80 |
|  | 10 | 98 |
| DL-BABA | 2 | 0 |
|  | 4 | 0 |
|  | 6 | 10 |
|  | 8 | 10 |
|  | 10 | 10 |

EXAMPLE 18

Following the method of Example 16, but running field trials in both Alpha and Bintje cultivars, the results are shown in Table 12.

TABLE 12

Percentage Control of Late Blight Epidemics Induced by *Phytophthora infestans* (Isolate MR1) in Potato Crops Treated with BABA (25 WP) in Three Independent Field Experiments

| Experiment & Cultivar | Dose (Kg a.i. per ha) | Interval between Sprays (Days) | | |
|---|---|---|---|---|
|  |  | 7 | 10 | 14 |
| Autumn Alpha | 0 | — | — | 0 |
|  | 0.2 | — | — | 24.6 |
|  | 0.4 | — | — | 52.6 |
|  | 0.8 | — | — | 55.1 |
| Winter Bintje | 0 | 0 | 0 | 0 |
|  | 0.2 | 55.0 | 42.1 | 38.4 |
|  | 0.4 | 57.4 | 52.5 | 47.1 |
|  | 0.8 | 62.6 | 62.6 | 58.0 |
| Spring Alpha | 0 | 0 | — | — |
|  | 0.57 | 38.0 | — | — |
|  | 1.15 | 77.7 | — | — |
|  | 2.30 | 75.0 | — | — |
| Spring Bintje | 0 | 0 | — | — |
|  | 0.57 | 35.2 | — | — |
|  | 1.15 | 64.5 | — | — |
|  | 2.30 | 76.0 | — | — |

EXAMPLES 19–20

Resistance to *P. tabacina* induced in tobacco plants was studied as outlined by Cohen (*Physiol. and Molec. Plant Path*. 44:273–288, 1994) where the active ingredients were applied as a stem injection or foliar spray. Results are shown in Table 13.

TABLE 13

Resistance to *Peronosporo tabacina* in Tobacco Plants by Amninobutyric Acids

| Compound | Foliar Spray (% Protection) | Stem Injection[c] Disease Severity (mean ± SD) |
|---|---|---|
| Water | 0 | $2.0 \pm 0^a$ |
| DL-AABA | 10 | $1.3 \pm 0.2^b$ |
| DL-BABA | 78 | $0.7 \pm 0.2^c$ |
| R-BABA | 99 | $0.07 \pm 0.09^d$ |
| GABA | −2 | $2.0 \pm 0^a$ |
| SA[a] | 80 | $1.5 \pm 0^b$ |
| INA[b] | 61 | $0.5 \pm 0^c$ |

[a]Sodium salicylate
[b]2,6 dichloro-iso-nictonic acid
[c]The letters refer to statistics

EXAMPLE 21

Following the methods of Examples 19–20, the effects of a soil drench with DL-BABA (3 mg per plant) on blue mold development in tobacco cv. Ky 16 showed an 80% control of the disease some 20 days after challenge inoculations.

EXAMPLE 22

Sunflower plants were protected against downy mildew caused by *P. halstedii* by treating the seeds with BABA. Thus, the seeds were soaked for 24 hours in a solution containing 10 mg BABA per ml, and then sown in pots in a greenhouse. Two weeks later, the developed plants were inoculated with *P. halstedii*. The progress of the disease was assessed after seven more days with the following results: while the control had 100% of the plants remaining infected, the treated plants had only a 2% rate of infection.

EXAMPLE 23

Maize (Line 3376) seeds were allowed to sprout in water for five days. They were then dipped in a BABA solution for one day. The sprouted seeds were washed and placed in contact with *Fusarium moniliforme* for one day and then planted in pots. After two weeks, the progress of the disease was as follows:

| BABA (ppm) | 0 | 125 | 250 | 500 | 2000 |
|---|---|---|---|---|---|
| % Plants Infected | 70 | 80 | 40 | 0 | 0 |

EXAMPLE 24

The activity of N-benzoyl-3-aminobutyric acid n-octyl ester against late blight (*P. infestans*) on potato in a growth chamber was studied. Six-week-old plants in pots were sprayed with the compounds and inoculated two days later. Disease records taken seven days post-inoculations are listed in Table 14.

TABLE 14

Activity of N-benzoyl-e-aminobutyric Acid N-octyl Ester against Late Blight (*Phytophthora infestans*) on Potato in Growth Chambers

| Concentration ppm | % Protection |
|---|---|
| 500 | 77 |
| 1000 | 89 |
| 2000 | 96 |

EXAMPLE 25

The effect of BABA against grey mold in tomato and cucumber was studied. Young tomato plants (cultivar Baby) (4-leaf stage) and young cucumber plants (cultivar Dlila) (1-leaf stage) were sprayed with BABA and inoculated two days later with a spore suspension of *Botrytis cinera*. The plants were kept under a moist Perspex® cover in a growth chamber for four days and then monitored for infection. The results are listed in Table 15.

TABLE 15

The Effects of BABA against Grey Mold, Caused by *Botrytis cinerea*, in Tomato and Cucumber

| BABA Concentration | % Plants Infected | |
|---|---|---|
| (ppm) | Tomato | Cucumber |
| 0 | 100 | 100 |
| 62 | 20 | 50 |
| 125 | 0 | 30 |
| 200 | 0 | 0 |
| 500 | 0 | 0 |
| 1000 | 0 | 0 |
| 2000 | 0 | 0 |

EXAMPLE 26

Preparation of N-benzoyl-3-aminobutyric Acid-1-methyl-1-butylester

The mixture of 2.0 g n-benzoyl-e-aminobutyric acid, 1.5 g 2-pentanol, 30 ml toluene and 0.004 g $H_2SO_4$ (conc.) was heated under reflux for 6.5 hours. The water formed in the remission was separated by azeotropic distillation. The cooled solution was washed with water (3×15 ml) and with 2% sodium bicarbonate (3×5 ml). After the evaporation of the solvent and distillation of the excess alcohol at 30° C. (0.4 mm Hg), 2.5 g oily product was obtained. The structure was confirmed by mass spectroscopy and NMR spectroscopic methods. By proceeding as described above, using the suitable mass spectroscopy and starting materials, compounds 2 to 8 were prepared.

EXAMPLE 27

Preparation of N-benzyl-3-aminobutyric Acid-1-methyl-l-pentyl Ester 37.2 g benzylamine was added to 30 g crotonic acid dissolved in 120 g ethyl alcohol at 10–15° C. during 25 minutes. The mixture was heated at 75–77° C. for five hours. The reaction was cooled to room temperature and n-benzyl-e-aminobutyric acid was filtered to afford 43.8 g.

Thionyl chloride (2.4 g) was added to 4.0 g of the benzyl product in 50 ml toluene at room temperature during 15 minutes. The mixture was heated at 80° C. for one hour. After cooling, 17.2 g 2-hexanol was added at room temperature during 15 minutes. The reaction was heated at 80° C. for four hours. The mixture was washed with 2×50 ml water and 3×50 ml 2% sodium bicarbonate. After evaporation and distillation of the excess alcohol, 4.4 g of compound was obtained. By further purification on a silica gel column using a mixture of dichloroethane:ethyl acetate (90:10) as eluant, 3.2 g of ester was obtained.

The structure was proved by NMR and mass spectroscopy. By proceeding as described above, using suitable starting materials, compounds 10 and 11 were prepared.

EXAMPLE 28

Preparation of β-aminobutyric Acid Hydrochloride 6.0 g β-aminobutyric acid was dissolved in 20 ml water. After the addition of 8.0 g ml 32, the solution was evaporated, and the compound was dried.

EXAMPLE 29

Preparation of β-amino Butyric Acid Sodium Salt 6.0 g β-aminobutyric acid was dissolved in 20 ml water. 2.3 g NaOH, dissolved in 12 ml water, was added. The solution was evaporated, and the solid was dried.

EXAMPLE 30

The activity of some BABA derivatives against powdery mildew caused by *Erysiphe graminis* in wheat, eight days after inoculation was studied. The results are shown in Table 16, which is to be compared with the case without any treatment, which showed only a 12% efficacy of control.

TABLE 16

Activity of Some BABA Derivatives against Powdery Mildew Caused by *Erysiphe graminis* in Wheat (8 days after inoculation; dose: 1000 ppm)

$CH_3C(H)NHR_6CH_2C(O)OR_3$

| Compound No. | $R_6$ | $R_3$ | % Efficacy of Control |
|---|---|---|---|
| 9 | $C_6H_5CH_2$ | $CH(CH_3)(CH_2)_3CH_3$ | 77 |
| 10 | $C_6H_5CH_2CH_2$ | $(CH_2)_7CH_3$ | 71 |
| 11 | $C_6H_5CH_2CH_2$ | $CH(CH_3)(CH_2)_3CH_3$ | 80 |
| 12 | H | H | 71 |
| 13 | H | Na | 91 |

EXAMPLE 31

Following the above-described methods, the activity of some BABA derivatives against late blight caused by *P. infestans* in tomato was studied. The results are shown in Table 17, which is to be compared with the case without any treatment, which showed only a 5% efficacy of control.

TABLE 17

Activity of Some BABA Derivatives against Late Blight
Caused by *Phytophthora Infestans* in Tomato
(4 days after inoculation; dose: 1000 ppm)

$CH_3C(H)NHR_6CH_2C(O)OR_3$

| Compound No. | $R_6$ | $R_3$ | % Efficacy of Control |
|---|---|---|---|
| 10 | $C_6H_5CH_2CH_2$ | $(CH_2)_7CH_3$ | 77 |
| 11 | $C_6H_5CH_2CH_2$ | $CH(CH_{31})(CH2)_3CH_3$ | 77 |
| 12 | H | H | 87 |
| 13 | H | Na | 92 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A compound of formula (I)

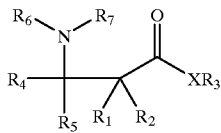

wherein:
(a) $R_1$ and $R_2$ are independently hydrogen, $C_{1-8}$ alkyl phenyl, and phenyl $C_{1-4}$ alkyl;
(b) $R_3$ is $C_{1-23}$ straight or branched alkyl, carboxy $C_{1-4}$ alkyl, phenyl $C_{1-4}$ alkyl, wherein the phenyl moiety is unsubstituted or monosubstituted by halogen, $C_{2-23}$ alkoxycarbonyl $C_{1-4}$ alkyl;
(c) $R_4$ is methyl or $C_{1-8}$ substituted methyl;
(d) $R_5$ is hydrogen or $C_{1-8}$ straight or branched alkyl,
(e) $R_6$ is hydrogen, $C_{1-8}$ straight or branched alkyl $C_{2-8}$ alkanoyl, phenyl $C_{1-4}$, alkyl, benzoyl, wherein the phenyl moiety is unsubstituted or monosubstituted with halogen, $C_{2-8}$ alkyl, phenyl, phenyl $C_{1-4}$ alkyl; phenyl $C_{2-4}$ alkyloxycarbonyl; $R_7$ is benzoyl
(f) X is O, S or NH, and salts thereof.

2. A compound according to claim 1, wherein $R_1$ and $R_2$ are independently hydrogen, methyl or phenyl; $R_3$ is $C_{1-23}$ straight or branched alkyl; $R_4$ and $R_5$ are independently hydrogen or $C_{1-3}$ alkyl; $R_6$ and $R_7$ are independently hydrogen, alkyl or haloalkyl optionally substituted by phenyl, benzyl and benzoyl, $C_{1-6}$ alkyl or benzyl optionally substituted by halogen; and Z is oxygen.

3. The compound according to claim 1, which is N-benzoyl-3-aminobutyric acid 1-methyl-1-butyl ester.

4. The compound according to claim 1, which is N-benzoyl-3-aminobutyric acid 1-methyl-5-pentyl ester.

5. The compound according to claim 1, which is N-benzoyl-3-aminobutyric acid n-heptyl ester.

6. The compound according to claim 1, which is N-benzoyl-3-aminobutyric acid n-hexyl ester.

7. The compound according to claim 1, which is N-benzoyl-3-aminobutyric acid 1-methyl-1-heptyl ester.

8. The compound according to claim 1, which is N-benzoyl-3-aminobutyric acid 1-methyl-1-hexyl ester.

9. The compound according to claim 1, which is N-benzoyl-3-aminobutyric acid 1-methyl-1-octyl ester.

10. The compound according to claim 1, which is N-benzoyl-3-aminobutyric acid 1-methyl-1-pentyl ester.

11. The compound according to claim 1, which is N-benzoyl-3-aminobutyric acid 1-methyl-5-pentyl ester.

12. A method for protecting a crop against fungal diseases caused by fungi by inducing local and systemic resistance of said crop and by conventional means comprising applying to the crop or its locus a composition an effective amount of at least one compound of formula (I):

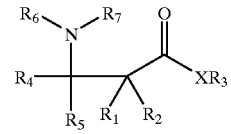

wherein:
(a) $R_1$ and $R_2$ are independently hydrogen, $C_{1-8}$ alkyl phenyl, and phenyl $C_{1-4}$ alkyl;
(b) $R_3$ is $C_{1-23}$ straight or branched alkyl, carboxy $C_{1-4}$ alkyl, phenyl $C_{1-4}$ alkyl, wherein the phenyl moiety is unsubstituted or monosubstituted by halogen, $C_{2-23}$ alkoxycarbonyl $C_{1-4}$ alkyl, or salts such as sodium;
(c) $R_4$ is methyl or $C_{1-8}$ substituted methyl;
(d) $R_5$ is hydrogen or $C_{1-8}$ straight or branched alkyl,
(e) $R_6$ and $R_7$ are independently hydrogen, $C_{1-8}$ straight or branched alkyl $C_{2-8}$ alkanoyl, phenyl $C_{1-4}$, alkyl, benzoyl, wherein the phenyl moiety is unsubstituted or monosubstituted with the halogen, $C_{2-8}$ alkoxycarbonyl; $CONHR_8$, wherein $R_8$ is hydrogen, $C_{1-8}$ alkyl; phenyl, phenyl $C_{1-4}$ alkyl; phenyl $C_{2-4}$ alkyloxycarbonyl;
(f) X is O, S or NH, or salts thereof, and the crop is selected from the group consisting of corn, cucumber, melon, broccoli, cauliflower, kohlrabi, sunflower, potato, tobacco, grape, cotton, cabbage, maize, sorghum, pearl millet, rice, cereals, lettuce, hop, avocado, citrus, soybean and onion in an amount sufficient to induce local and system resistance of the crop to control the fungal disease; provided that when $R_5$=H and $R_4$=$CH_3$, $R_3$ cannot be octyl.

13. A method according to claim 12, wherein $R_1$ and $R_2$ are independently hydrogen, methyl or phenyl; $R_3$ is $C_{1-23}$ straight or branched alkyl; $R_4$ and $R_5$ are independently hydrogen or $C_{1-3}$ alkyl; $R_6$ and $R_7$ are independently hydrogen, alkyl or haloalkyl optionally substituted by phenyl, benzyl and benzoyl, $C_{1-6}$ alkyl or benzyl optionally substituted by halogen; and X is oxygen.

14. A method according to claim 12, wherein the crop is selected from the group consisting of cucumber, melon, broccoli, cauliflower, kohlrabi, potato, sunflower, tobacco, grape, cotton, maize, sorghum, cabbage, pearl millet, rice, hop and cereals.

15. A method according to claim 12, wherein the crop is selected from the group consisting of sunflower, grape, cucumber, melon, broccoli, kohlrabi, cauliflower, potato, tobacco and maize.

16. A method according to claim 12, wherein the compound is applied to the leaves or stems of the plant.

17. A method according to claim 12, wherein the compound is applied to the roots of the plant.

18. A method according to claim 12, wherein the compound is applied to the soil.

19. A method according to claim 12, wherein the compound is applied to the seeds, tubers or bulbs of the plant.

20. A method according to claim 12, wherein the compound is applied pre-emergence.

21. A method according to claim 12, wherein the compound is applied post-emergence.

22. A method according to claim 12, wherein the compound is applied to the crop at a dosage rate of from 0.1 to 5 kg/ha.

23. A method according to claim 12, wherein the compound is applied to the crop at a dosage rate of 0.2 to 2 kg/ha.

24. A method according to claim 12, wherein the compound of formula (I) is -N-benzoyl-1-aminobutyric acid 1-methyl-1-butyl ester.

25. A method according to claim 12, wherein the compound of formula (I) is -N-benzoyl-3-aminobutyric acid 1-methyl-5-pentyl ester.

26. A method according to claim 12, wherein the compound of formula (I) is -N-benzoyl-3-aminobutyric acid n-heptyl ester.

27. A method according to claim 12, wherein the compound of formula (I) is -N-benzoyl-3-aminobutyric acid n-hexyl ester.

28. A method according to claim 12, wherein the compound of formula (I) is -N-benzoyl-3-aminobutyric acid 1-methyl-1-heptyl ester.

29. A method according to claim 12, wherein the compound of formula (I) is -N-benzoyl-3-aminobutyric acid 1-methyl-1-hexyl ester.

30. A method according to claim 12, wherein the compound of formula (I) is -N-benzoyl-3-aminobutyric acid 1-methyl-1-octyl ester.

31. A method according to claim 12, wherein the compound of formula (I) is -N-benzoyl-3-aminobutyric acid 1-methyl-1-pentyl ester.

32. A method according to claim 12, wherein the compound of formula (I) is -N-benzoyl-3-aminobutyric acid 1-methyl-5-pentyl ester.

33. A method according to claim 12, wherein the compound of formula (I) is -N-benzoyl-2-phenylethyl-3-aminobutyric acid n-octyl ester.

34. A method according to claim 12, wherein the compound of formula (I) is -N-benzoyl-2-phenylethyl-3-aminobutyric acid 1-methyl-1-pentyl ester.

35. A method according to claim 12, wherein the compound of formula (I) is -13-aminobutyric acid hydrochloride.

36. A method according to claim 12, wherein the compound of formula (I) is -3-aminobutyric acid sodium salt.

37. A method of protecting wheat against powdery mildew by inducing local and systemic resistance of the wheat and by conventional means comprising applying to the wheat plant or its locus an effective amount of at least one compound of formula (I):

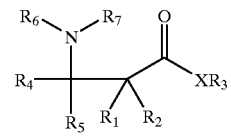

wherein:

(a) $R_1$ and $R_2$ are independently hydrogen, $C_{1-8}$ alkyl phenyl, and phenyl $C_{1-4}$ alkyl;

(b) $R_3$ is $C_{1-23}$ straight or branched alkyl, carboxy $C_{1-4}$ alkyl, phenyl $C_{1-4}$ alkyl, wherein the phenyl moiety is unsubstituted or monosubstituted by halogen, $C_{2-23}$ alkoxycarbonyl $C_{1-4}$ alkyl, or salts such as $Na^+$;

(c) $R_4$ is methyl or $C_{1-8}$ substituted methyl;

(d) $R_5$ is hydrogen or $C_{1-8}$ straight or branched alkyl, (e) $R_6$ and $R_7$ are independently hydrogen, $C_{1-8}$ straight or branched alkyl $C_{2-8}$ alkanoyl, phenyl $C_{1-4}$, alkyl, benzoyl, wherein the phenyl moiety is unsubstituted or monosubstituted with halogen, $C_{2-8}$ alkoxycarbonyl; $CONHR_8$, wherein $R_8$ is hydrogen, $C_{1-8}$ alkyl; phenyl, phenyl $C_{1-4}$ alkyl; phenyl $C_{2-4}$ alkyloxycarbonyl;

(f) X is O, S or NH, or salts thereof.

38. The method according to claim 37, wherein the compound is applied to the leaves or stems of the plant.

39. The method according to claim 37, wherein the compound is applied to the roots of the plant.

40. The method according to claim 37, wherein the compound is applied to the soil.

41. The method according to claim 37, wherein the compound is applied to the seeds, tubers or bulbs of the plant.

42. The method according to claim 37, wherein the compound is applied pre-emergence.

43. The method according to claim 37, wherein the compound is applied post-emergence.

44. The method according to claim 37, wherein the compound is applied to the crop at a dosage rate of from 0.1 to 5 kg/ha.

45. The method according to claim 37, wherein the compound is applied to the crop at a dosage rate of 0.2 to 2 kg/ha.

46. The method according to claim 37, wherein the compound is N-benzyl-3-aminobutyric acid-1-methyl-1-pentyl ester.

47. The method according to claim 37, wherein the compound is N-2-phenylethyl-3-aminobutyric acid-n-octyl ester.

48. The method according to claim 37, wherein the compound is N-2-phenylethyl-3-aminobutyric acid-1-methyl-1-pentyl ester.

49. The method according to claim 37, wherein the compound is 13-aminobutyric acid hydrochloride.

50. The method according to claim 37, wherein the compound is 3-aminobutyric acid sodium salt.

51. A method of protecting potato against late blight by inducing local and systemic resistance of the potatoes and by conventional means comprising applying to the potato plant or its locus an effective amount of at least one compound of formula (I):

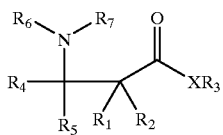

wherein:
(a) $R_1$ and $R_2$ are independently hydrogen, $C_{1-8}$ alkyl phenyl, and phenyl $C_{1-4}$ alkyl;
(b) $R_3$ is $C_{1-23}$ straight or branched alkyl, carboxy $C_{1-4}$ alkyl, phenyl $C_{1-4}$ alkyl, wherein the phenyl moiety is unsubstituted or monosubstituted by halogen, $C_{2-23}$ alkoxycarbonyl $C_{1-4}$ alkyl, or salts such as $Na^+$;
(c) $R_4$ is methyl or $C_{1-8}$ substituted methyl;
(d) $R_5$ is hydrogen or $C_{1-8}$ straight or branched alkyl,
(e) $R_6$ and $R_7$ are independently hydrogen, $C_{1-8}$ straight or branched alkyl $C_{2-8}$ alkanoyl, phenyl $C_{1-4}$, alkyl, benzoyl, wherein the phenyl moiety is unsubstituted or monosubstituted with halogen, $C_{2-8}$ alkoxycarbonyl; $CONHR_8$, wherein $R_8$ is hydrogen, $C_{1-8}$ alkyl; phenyl, phenyl $C_{1-4}$ alkyl; phenyl $C_{2-4}$ alkyloxycarbonyl;
(f) X is O, S or NH, or salts thereof.

52. The method according to claim 51, wherein the compound is applied to the leaves or stems of the plant.

53. The method according to claim 51, wherein the compound is applied to the roots of the plant.

54. The method according to claim 51, wherein the compound is applied to the soil.

55. The method according to claim 51, wherein the compound is applied to the seeds, tubers or bulbs of the plant.

56. The method according to claim 51, wherein the compound is applied pre-emergence.

57. The method according to claim 51, wherein the compound is applied post-emergence.

58. The method according to claim 51, wherein the compound is applied to the crop at a dosage rate of from 0.1 to 5 kg/ha.

59. The method according to claim 51, wherein the compound is applied to the crop at a dosage rate of 0.2 to 2 kg/ha.

60. The method according to claim 51, wherein the compound is N-benzoyl-3-aminobutyric acid-1-methyl-1-butyl ester.

61. The method according to claim 51, wherein the compound is N-benzoyl-3-aminobutyric acid-1-methyl-5-pentyl ester.

62. The method according to claim 51, wherein the compound is N-benzoyl-3-aminobutyric acid-n-heptyl ester.

63. The method according to claim 51, wherein the compound is N-benzoyl-3-aminobutyric acid-n-hexyl ester.

64. The method according to claim 51, wherein the compound is N-benzoyl-3-aminobutyric acid-1-methyl-1-heptyl ester.

65. The method according to claim 51, wherein the compound is N-benzoyl-3-aminobutyric acid-1-methyl-hexyl ester.

66. The method according to claim 51, wherein the compound is N-benzoyl-3-aminobutyric acid-1-methyl-octyl ester.

67. The method according to claim 51, wherein the compound is N-benzoyl-3-aminobutyric acid-1-methyl-pentyl ester.

68. The method according to claim 51, wherein the compound is N-2-phenylethyl-3-aminobutyric acid-n-octyl ester.

69. The method according to claim 51, wherein the compound is N-2-phenylethyl-3-aminobutyric acid-1-methyl-1-pentyl ester.

70. The method according to claim 51, wherein the compound is 13-aminobutyric acid.

71. The method according to claim 51, wherein the compound is 3-aminobutyric acid sodium salt.

72. A method of protecting tomato against *Phytopythora infestans* by inducing local and systemic resistance of the tomatoes and by conventional means comprising applying to the tomato plant or its locus an effective amount of at least one compound of formula (I):

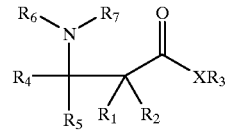

wherein:
(a) $R_1$ and $R_2$ are independently hydrogen, $C_{1-8}$ alkyl phenyl, and phenyl $C_{1-4}$ alkyl;
(b) $R_3$ is $C_{1-23}$ straight or branched alkyl, carboxy $C_{1-4}$ alkyl, phenyl $C_{1-4}$ alkyl, wherein the phenyl moiety is unsubstituted or monosubstituted by halogen, $C_{2-23}$ alkoxycarbonyl $C_{1-4}$ alkyl, or salts such as $Na^+$;
(c) $R_4$ is methyl or $C_{1-8}$ substituted methyl;
(d) $R_5$ is hydrogen or $C_{1-8}$ straight or branched alkyl,
(e) $R_6$ and $R_7$ are independently hydrogen, $C_{1-8}$ straight or branched alkyl $C_{2-8}$ alkanoyl, phenyl $C_{1-4}$, alkyl, benzoyl, wherein the phenyl moiety is unsubstituted or monosubstituted with halogen, $C_{2-8}$ alkoxycarbonyl; $CONHR_8$, wherein $R_8$ is hydrogen, $C_{1-8}$ alkyl; phenyl, phenyl $C_{1-4}$ alkyl; phenyl $C_{2-4}$ alkyloxycarbonyl;
(f) X is O, S or NH, or salts thereof.

73. The method according to claim 72, wherein the compound is applied to the leaves or stems of the plant.

74. The method according to claim 72, wherein the compound is applied to the roots of the plant.

75. The method according to claim 72, wherein the compound is applied to the soil.

76. The method according to claim 72, wherein the compound is applied to the seeds, tubers or bulbs of the plant.

77. The method according to claim 72, wherein the compound is applied pre-emergence.

78. The method according to claim 72, wherein the compound is applied post-emergence.

79. The method according to claim 72, wherein the compound is applied to the crop at a dosage rate of from 0.1 to 5 kg/ha.

80. The method according to claim 72, wherein the compound is applied to the crop at a dosage rate of 0.2 to 2 kg/ha.

81. The method in accordance with claim 72, wherein the compound is N-2-phenylethyl-3-aminobutyric acid-n-octyl ester.

82. The method in accordance with claim 72, wherein the compound is N-2-phenylethyl-3-aminobutyric acid-1methyl-1-pentyl ester.

83. The method in accordance with claim 72, wherein the compound is 13-aminobutyric acid.

84. The method in accordance with claim 72, wherein the compound is 3-aminobutyric acid sodium salt.

* * * * *